United States Patent [19]

Davies et al.

[11] 4,144,327

[45] Mar. 13, 1979

[54] ANTIMICROBIAL COMPOSITION COMPRISING LYTIC ENZYMES FROM PHYSARUM AND AN ANTIMYCOTIC AGENT

[75] Inventors: David A. L. Davies; Anthony M. S. Pope, both of High Wycombe, England

[73] Assignee: G. D. Searle & Co., Chicago, Ill.

[21] Appl. No.: 888,276

[22] Filed: Mar. 20, 1978

[51] Int. Cl.² .................. A61K 37/48; A61K 31/71
[52] U.S. Cl. .................................. 424/94; 424/181
[58] Field of Search ........................................ 424/94

[56] References Cited

PUBLICATIONS

Kawakami et al.–Chem. Abst., vol. 82, (1975), p. 152,074h.

*Primary Examiner*—Sam Rosen
*Attorney, Agent, or Firm*—John J. McDonnell; Mary Jo Kanady

[57] ABSTRACT

The present invention encompasses an antimicrobial composition comprising an extract of lytic enzymes from Physarum. These lytic enzymes are particularly effective antimycotic agents when used in conjunction with conventional antimycotic agents.

5 Claims, No Drawings

ANTIMICROBIAL COMPOSITION COMPRISING LYTIC ENZYMES FROM PHYSARUM AND AN ANTIMYCOTIC AGENT

The present invention encompasses an antimicrobial composition comprising an extract of lytic enzymes from Physarum. This invention encompasses a crude extract from Physarum having chitinase, $\alpha$-1,3 glucanase, $\alpha$-1,4 glucanase, $\alpha$-1,6-glucanase, $\beta$-1,3 glucanase, $\beta$-1,6 glucanase, $\beta$-glucosidase, $\beta$-galactosidase, $\beta$-mananase, chitiobiase, $\alpha$-glucosidase, and muramidase enyzme activity and a purified extract from Physarum having $\alpha$-1,3 glucanase, $\alpha$-1,4 glucanase, $\alpha$-1,6 glucanase, $\beta$-1,3 glucanase, $\beta$-1,6 glucanase, $\beta$-glucosidase, $\beta$-galactosidase, $\beta$-mannanse and chitobiase enzyme activity. The present invention also encompasses a pharmaceutical composition suitable for combining with a pharmaceutically acceptable carrier said composition comprising a sterile, pyrogen free, lyophilized extract of lytic enzymes from Physarum. The present invention also encompasses the above formulations suitable for parenteral or topical application and further containing a conventional antimycotic agent such as Amphotericin-B, Nystatin, or 5-fluorocytosine as well as other agents named in Chapter 12 of Cuttings Handbook of Pharmacology 4th edition, Appleton-Century-Crofts, N.Y., N.Y. pages 79–85.

The compositions of the present inventions provide an adjunct to conventional antimycotic chemotherapy by partially degrading fungal cell walls and thereby making fungal cells more susceptible to conventional antimycotic therapy. Therefore the present invention is concerned with a method of treating mycoses which involves alternate or simultaneous administration of Physarum extract and antimycotic agent.

In the context of the present invention the term therapeutically effective amount refers to the amount of Physarum extract which is effective alone or effective in conjunction with a conventional antimycotic agent such as Amphotericin-B. An antimycotic agent which is ineffective alone or toxic at effective doses can be made effective at less than therapeutic doses by compositions of the present invention. Those skilled in the pharmaceutical arts will recognize that doses will be varied depending on the severity of the infection and individual patient response. Typically an intravenous dose of 2 mg/kg every 12 hours for 4 days in conjunction with Amphotericin-B therapy is an effective dose.

Typically an enzyme extract precipitated by 1–5 volumes of 95% ethanol from Physarum culture growth has Chitinase
$\alpha$-1,3 glucanase
$\alpha$-1,4 glucanase
$\alpha$-1,6 glucanase
$\beta$-1,3 glucanase
$\beta$-1,6 glucanase
$\beta$-glucosidase
$\beta$-galactosidase
$\beta$-mannanase
Chitobiase enzyme activity.

These enzxymes are lyophilized for administration in sterile pyrogen free solutions. For example, 2 mg/kg of body weight of this preparation is administered in 200 ml of 5% dextrose over 1–2 hours twice daily for 4 days in conjunction with Amphotericin B therapy for lung coccidiomycosis or aspergillus infection.

Compounds and methods of the present invention are particularly effective in treating Candida, Aspergillus and Trichophyton infections such as those caused by *Candida albicans, Aspergillus fumigatus* ad *Trichophyton mentagrophytes*.

Injectable, intravenous, and topical formulations are prepared as described in Remington's Pharmaceutical Science Mach Publishing Company, Easton, Pennsylvania 1965 by art recognized techniques. Those skilled in the pharmaceutical arts will recognize a wise variety of dosage forms and formulations.

Chemical abstracts 78 157874W (1973) describes cell wall degrading enzymes extracted from a growth of *Physarum polycephalum* cultivated together with yeast or bacteria. The resulting enzymes were shown to degrade yeast cell walls. The present invention involves crude and purified extracts of cultures of Physarum alone, pharmaceutical compositions thereof and the use of these compositions as an adjunct in therapy of mycoses.

U.S. Pat. No. 3,682,778 describes methods for extracting cell lytic enzymes from various Coprinus species. M.V. Tracey, Biochem Journal 61, 579–588 (1955) discloses extracts of certain Lycoperdon species and compares the chitinase activity of these to chitinase activity of Coprinus extracts.

British Patent specification Nos. 1,048,887 and 1,410,079 describe bacterial sources of cell lytic enzymes and their in vitro activity against pathogenic fungi and Kokai et al. Chem. Abs. 79, 133662 V describes $\beta$, 1-3 glucanase and chitinase as fungicide for rice blight. Mirua, Tohoku Journal of Exp. Med. 59, N. 4,403 (1954) suggests that in vitro activity of bacterial chitinase might indicate its use as a topical anti-dermatomycosis agent, but this was not tested.

It has been found that lytic enzyme mixtures extracted from physarum species not only have significantly greater antimycotic activity than those extracted from Coprinus and Lycoperdon but in addition the Physarum enzyme extracts show a wider spectrum of activity deriving from their ability to attack not only fungal but also bacterial cell walls. This latter property is thought to arise because of the presence of muramidase in the crude enzyme extract, an enzyme not present in significant amounts in extracts from Coprinus or Lycoperdon.

U.S. Pat. No. 4,062,941 describes the use of cell lytic enzymes from Coprinus and Lycoperdon whereas the present invention is concerned with medicinally useful extracts from Physarum.

The preferred source of enzyme extract is *Physarum polycephalum*. The desired enzyme extract is most conveniently obtained by growth in liquid culture, separating the supernatant liquid from the culture and isolating the product from this liquid.

In a preferred method *Physarum polycephalum* is grown under aerobic conditions in shake flasks or in a stirred fermenter in a liquid medium of the following composition:

| | | |
|---|---|---|
| Glucose | 10 | g |
| Bactopeptone | 10 | g |
| Citric Acid H$_2$O | 3.54 | g |
| KH$_2$PO$_4$ | 2.0 | g |
| CaCl$_2$6H$_2$O | 0.9 | g |
| Mg SO$_4$ 7H$_2$O | 0.6 | g |
| Na$_2$EDTA | 0.224 | g |

| -continued | | |
|---|---|---|
| FeCl$_2$4H$_2$O | 0.06 | g |
| ZnSO$_4$ 7H$_2$O | 0.034 | g |
| Thiamine HCl | 0.0424 | g |
| Biotin | 0.005 | g |
| Haemin | 0.005 | g |
| Distilled Water to | 1 liter | |

The glucose can be replaced by maltose, starch, galactose, or other suitable carbohydrate.

The medium is adjusted to pH 5 with 10% NaOH.

Preferred growth conditions are as follows: pH should be maintained at from 4.5 to 6, the optimum pH being 5; the required temperature is from 25° to 29° C. and continuous very high oxygenation is desirable.

Enzyme release increases with cell numbers up to late exponential phase and continues to rise thereafter, but at a reduced rate. For optimal enzyme production and minimal extracellular polysaccharide (which complicates extraction) cultures are harvested after approximately 180-200 hours growth. The crude enzyme extract is obtained as follows:

Culture supernatant is separated from the cells, for example by centrifugation (1600 xg for 20 minutes). The solid residue is discarded. The separated supernatant is cooled and residual slime precipitated for example by the addition of ammonium sulfate to 25% saturation or by the addition of 1 volume of ethanol or acetone previously cooled to −20° C. The precipitate is separated from the liquor, for example by centrifugation at 10,000 xg for 30 minutes and the residue discarded. The liquid is dialysed against several changes of distilled water and lyophilised. This is the crude extract which can, if desired, be further purified by conventional methods such as membrane filtration, gel filtration or affinity chromotography.

A typical crude extract from *Physarum polycephalum* has the following profile of enzyme activity:

| Chitinase | 0.0008 | μ |
|---|---|---|
| β-1,3 glucanase | 0.28 | μ |
| β-1,6 glucanase | 0.02 | μ |
| α-1,6 glucanase | 0.004 | μ |
| α-1,3, α1,4 glucanase | 0.03 | μ |
| β-glucosidase | 0.14 | μ |
| Chitobiase | 0.113 | μ |
| β-galactosidase | 0.17 | μ |
| β-Mannanase | 0.03 | μ |
| β-1,4 glucanase | .02 | μ |
| α-glucosidase | .06 | μ |
| α-1,4 glucanase | .03 | μ |
| Muramidase | 100 | μ |

A purified sample precipitated between 1 and 5 volumes of 95% ethanol has the following enzyme profile:

| Chitinase | 0.02 | μ |
|---|---|---|
| β-1,3 glucanase | 0.49 | μ |
| β-1,6 glucanase | 0.07 | μ |
| α-1,6 glucanase | 0.02 | μ |
| α-1,3, α1,4 glucanase | 0.04 | μ |
| β-glucosidase | 0.35 | μ |
| Chitobiase | 0.25 | μ |
| β-galactosidase | 0.35 | μ |
| β-Mannanase | 0.06 | μ |

(u) Unit — the amount of enzyme that will release 1 u Mole of product/1 minute/1 mg protein at 37° C.

The physarum extract is of low toxicity. Female BALB/c mice weighing from 20-25g were injected i.p. with purified extract (purified by precipitation with 4 vols. of ethanol) at doses of from 0 to 800mg/kg. in saline. Mice were observed for 7 days and deaths recorded as they occurred. LD$_{50}$ was calculated by plotting survivors against dose and deaths against dose, the LD$_{50}$ being the intersection of the curves. An LD$_{50}$ of 670 mg/kg was observed.

In rhesus monkeys toxicity tests established that no ill-effects were shown when the animals were given a dose approximately ten times the expected human dose of Physarum extract in saline. Respiration, pulse and heart rate, biochemistry and haematology remained within normal tolerances.

The invention is further illustrated by the following examples:

EXAMPLE 1

The effects of Physarum extract, with or without conventional antimycotic drugs in inhibiting growth of *Candida albicans* in vitro was assessed by a turbidimetric method.

1 × 10$^5$ cells of *C.albicans* were inoculated into bottles of broth containing various amounts of crude Physarum extract, antimycotic drugs or mixtures of the two. Samples of these suspensions were taken (T$_o$) and their turbidity measured in a spectrophotometer at 560nm. The cultures were incubated for 24 hours at 37° C. and the turbidity measured again (T$_{24}$) and compared with that of a control culture (T$_{24}$ control). The results are shown in Table I. The value for T$_{24}$ control was 0.61.

TABLE I

Effect of Physarum extract and antimycotic drugs on growth of *Candida albicans* in liquid culture. OD 560 (mean of 3)

| Concentration | 100μg/ml | 20μg/ml | 1.0 μg/ml | 0.2μg/ml | 0.02μg/ml |
|---|---|---|---|---|---|
| Amphotericin-B | 0 | 0.21 ± 0.04 | 0.33 ± 0.04 | 0.15 ± 0.03 | 0.69 ± 0.07 |
| Nystatin | 0.01 ± 0.01 | 0.03 ± 0.02 | 0.03 ± 0.02 | 0.03 ± 0.03 | 0.15 ± 0.04 |
| Physarum extract | 0.06 ± 0.04 | 0.13 ± 0.03 | 0.35 ± 0.06 | 0.57 ± 0.09 | 0.64 ± 0.08 |
| Concentration | 50μg + 50μg | 10μg + 10μg | 1μg + 1μg | 0.1μg + 0.1μg | 0.01μg + 0.01μg |
| Physarum + Amphotericin-B | 0 | 0 | 0 | 0 | 0 |
| Physarum + Nystatin | 0 | 0 | 0 | 0 | 0 |

These results show a clear synergism between the Physarum extract and the antimycotic drugs.

EXAMPLE 2

Effect of Physarum extract on *Aspergillus fumigatus* infection in mice. BALB/c mice were injected via the lateral tail vein with 0.2ml of a suspension containing approximately 5 × 10$^6$ spores of *A.fumigatus*. On the three days following infection, mice were treated by intraperitoneal injection with 0.2 ml saline (control); or with 0.2 ml saline containing 10μg Physarum extract and 1μg Amphotericin B; or with 0.2ml saline containing 10μg Physarum only; or with 0.2ml saline containing Amphotericin B only. The course of infection was followed daily. The results are given in Table II.

TABLE II

| Treatment | Survival (5 mice/group) days |
|---|---|
| None | 12.5 ± 1.6 |
| 3 × 10μg Physarum extract | 25.2 ± 2.3 |
| 3 × 1μg Amphotericin B | 14.4 ± 1.5 |
| 3 × (10μg Physarum extract + 1μg Amphotericin B) | all alive at day 50 |

These results show clearly that the Physarum extract alone is effective to an appreciable extent in controlling the infection, showing better results that are obtained with Amphotericin alone. The results obtained using the extract together with the antimycotic drug demonstrates a strongly synergistic action.

EXAMPLE 3

Treatment of superficial fungal infection in guinea pigs with Physarum extract with or without Nystatin.

The shaved backs of 25 guinea pigs were inoculated with 5mm squares of a culture of *Trichophyton mentagrophytes*, a common skin pathogen. Four days after inoculation, the animals were checked visually for signs of infection and samples of hair and skin taken and cultured, (These were $T_o$ controls taken to confirm infection). Treatment then commenced. All treatments were applied in "Carbopol" buffered gel at a rate of 0.5g/animal/day according to the following scheme. Each group contained 5 animals:

Group 1: Control — treated with placebo gel only
Group 2: Gel + 0.1% (w/w) Physarum extract
3: Gel + 0.5% (w/w) Physarum extract
4: Gel + 0.5% (w/w) Nystatin
5: Gel + Physarum 0.1% + Nystatin 0.05%

Treatment was continued for 5 days and further samples of skin and hair were taken and cultured. 5 samples were taken from each animal and the number of discrete colonies on each culture plate was counted, the number of colonies being approximately equivalent to the amount of viable fungus remaining on the animals. (These were $T_5$ samples). The results are given in Table III.

TABLE III

| Group | 1 | 2 | 3 | 4 | 5 |
|---|---|---|---|---|---|
| T Samples (% animals infected) | 100 | 100 | 100 | 100 | 100 |
| $T_5$ Samples (% animals infected) | 100 | 60 | 40 | 60 | 20 |
| Number of colonies from samples | 212 | 91 | 70 | 96 | 28 |

These results show a marked reduction in numbers of animals infected and numbers of fungal colonies developing as a result of all treatments. However, Group 3 (0.5% (w/w Physarum) and Group 5 (0.1% Physarum + 0.05 Nystatin) gave the best results again showing the synergism between the extract and Nystatin.

EXAMPLE 4

Measurement of antibacterial activity of Physarum extract as a function of reduction of turbidity of suspensions of cells of *Micrococcus lysodeikticus*.

The potential antibacterial activity of Physarum enzyme extract resulting from the muramidase activity of the extract was measured as the reduction in the optical density (at 570nm) of a suspension of lyophilised cells of *Micrococcus lysodeikticus*. Enzyme extract from Physarum (2mg/ml) was compared with an enzyme extract from Coprinus (2Mg/ml) species and with a series of standard lysozyme solutions (0–16μg/ml). The optical density (OD) was read at $T_o$ and at $T_2O_v$ (after 20 minutes incubation at 37° C.). The results are as follows:

| Lysozyme Standards | OD at 570 nm |
|---|---|
| 16μg/ml | 0.112 |
| 8μg/ml | 0.220 |
| 4μg/ml | 0.360 |
| 2 μg/ml | 0.408 |
| 1 μg/ml | 0.417 |
| $T_o$ Control | 0.476 |
| Coprinus | |
| $T_{20}$ | 0.456 |
| $T_o$ | 0.456 |
| Physarum | |
| $T_{20}$ | 0.120 |
| $T_o$ | 0.470 |

These results show that Coprinus extract has little or no muramidase activity whereas the Physarum extract at 2mg/ml shows a muramidase activity equivalent to approximately 15μg/ml of lysozyme, i.e. pure muramidase.

EXAMPLE 5

(1) 4 Groups of BALB/c mice were infected by intravenous injection of 0.2ml of suspension containing 5 × $10^6$ spores of *Aspergillus fumigatus* and treated in the 2 days following infection by intraperitoneal injection.

(a) 0.2ml saline 24 hrs. and 48 hrs. after infection (control)
(b) 0.2ml saline containing 200μg Physarum extract precipitated between 1 and 5 volumes of 95% ethanol at 24 hours and 0.2ml saline at 48 hrs.
(c) 0.2 ml saline at 24 hours, and 1 ug Amphotericin B 0.2 ml saline at 48 hrs.
(d) 200μg Physarum extract in 0.2 ml saline at 24 hours. 1 μg Amphotericin B in 0.2 ml saline at 48 hrs.

The course of infection was followed daily.

| | Mean Survival (days) | |
|---|---|---|
| Group (a) | 13.4 ± 1.14 | 12.6 ± 1.82 |
| (b) | 19.4 ± 1.52 | 14.6 ± 2.41 |
| (c) | 16.6 ± 2.07 | 15.0 ± 2.24 |
| (d) | All alive at 41 days and sacrificed for autopsy. | |

A strong synergistic effect is demonstrated between the Physarum extract and Amphotericin B.

At autopsy no abnormalities were found and no fungal activity was found. Some material from kidney tissue might have been fungal tissue, but not positive cultures were obtained.

EXAMPLE 6

(2) Similar experiment to Example 5. Six groups of 5 mice were infected intravenously with 5 × $10^6$ spores of *A.fumigatus* and treated 24 and 48 hrs. after infection by intraperitoneal injection with Physarum extract and with Amphotericin-B.

(a) 0.2 ml saline 24 and 48 hrs after infection (b) 0.2 ml saline at 24 hrs; 1μg of Amphotericin-B in 0.2 ml saline at 48 hrs.
(c) 100 μg Physarum extract precipitated between 1 and 5 volumes of 95% ethanol in 0.2 ml saline at 24 hrs; 0.2 ml saline at 48 hrs.
(d) 10 μg Physarum extract in 0.2 ml saline at 24 hrs; 0.2 ml saline at 48 hrs.
(e) 100 μg Physarum extract in 0.2 ml saline at 24 hrs; 1 μg Amphotericin B in 0.2 ml saline at 48 hrs.
(f) 10 μg Physarum extract in 0.2 ml saline at 24 hrs; 1 μg of Amphotericin B in 0.2 ml saline at 48 hrs.

|  | Mean Survival (days) |
|---|---|
| Group (a) | 14.0 ± 2.0 |
| (b) | 16.0 ± 2.55 |
| (c) | 16.2 ± 3.19 |
| (d) | 14.4 ± 2.07 |
| (e) | All alive at day 50 |
| (f) | 42.0 ± 2.74 |

Again, synergism between Physarum extract and Amphotericin B was demonstrated.

What is claimed is:

1. A method for treating fungal infections in animals comprising administering to an animal in need of anti-fungal treatment an effective amount of mycolytic enzymes extracted from Physarum.

2. A method for treating fungal infections in animals comprising administering to an animal in need of anti-fungal treatment an effective amount of mycolytic enzymes extracts from Physarum in conjunction with an antimycotic agent.

3. A method according to claim 2 for treating fungal infections in animals comprising administering to an animal in need of anti-fungal treatment an effective amount of mycolytic enzymes extracted from Physarum in conjunction with Amphotericin-B or Nystatin.

4. A pharmaceutical composition suitable for combining with a pharmaceutically acceptable carrier comprising an effective amount of a sterile pyrogen free, lyophilised extract of lytic enzymes from Physarum in combination with an effective amount of an antimycotic agent.

5. A pharmaceutical composition, according to claim 4, wherein the antimycotic agent is Amphotericin-B, Nystatin, or 5-fluorocystosine.

* * * * *